(12) United States Patent
Kanai et al.

(10) Patent No.: US 10,029,968 B2
(45) Date of Patent: Jul. 24, 2018

(54) PROCESS FOR PRODUCING ALCOHOL ANALOGUE

(71) Applicant: Takasago International Corporation, Tokyo (JP)

(72) Inventors: Motomu Kanai, Tokyo (JP); Shigeki Matsunaga, Hokkaido (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 15/514,405

(22) PCT Filed: Aug. 31, 2015

(86) PCT No.: PCT/JP2015/074733
§ 371 (c)(1),
(2) Date: Mar. 24, 2017

(87) PCT Pub. No.: WO2016/047388
PCT Pub. Date: Mar. 31, 2016

(65) Prior Publication Data
US 2017/0297990 A1    Oct. 19, 2017

(30) Foreign Application Priority Data
Sep. 26, 2014   (JP) ................. 2014-196358

(51) Int. Cl.
| | | |
|---|---|---|
| *C07C 45/45* | (2006.01) | |
| *B01J 31/24* | (2006.01) | |
| *C07F 9/36* | (2006.01) | |
| *B01J 31/22* | (2006.01) | |
| *B01J 31/02* | (2006.01) | |

(52) U.S. Cl.
CPC ........... *C07C 45/45* (2013.01); *B01J 31/0267* (2013.01); *B01J 31/22* (2013.01); *B01J 31/2414* (2013.01); *C07F 9/36* (2013.01); *B01J 2231/342* (2013.01); *B01J 2231/52* (2013.01); *B01J 2531/0241* (2013.01); *B01J 2531/0266* (2013.01); *B01J 2531/16* (2013.01); *B01J 2531/827* (2013.01); *C07B 2200/07* (2013.01)

(58) Field of Classification Search
None
See application file for complete search history.

(56) References Cited

PUBLICATIONS

Northrup et al., "The First Direct and Enantioselective Cross-Aldol Reaction of Aldehydes", J. Am. Chem. Soc. 2002, 124, 6798.
Northrup et al., "Two-Step Synthesis of Carbohydrates by Selective Aldol Reactions", Science, vol. 305, Sep. 17, 2004, 1752-1755.
Chowdari et al., "Proline-catalyzed asymmetric assembly reactions: enzyme-like assembly of carbohydrates and polyketides from three aldehyde substrates", Tetrahedron Letter 43, 2002, 9591-9595.
Cordova et al., "Amino Acid Catalyzed Neogenesis of Carbohydrates: A Plausible Ancleint Transformation", Chem. Eur. J., 2005, 11, 4772-4784.
Mangion et al., "The Importance of Iminium Geometry Control in Enamine Catalyst: Identification of a New Catalyst Architecture for Aldehyde-Aldehyde Couplings", Angew. Chem Int. Ed., 2004, 43, 6722-6724.
Hayashi et al., "A Diarylprolinol in an Asymmetric, Catalytic, and Direct Crossed-Aldol Reaction of Acetaldehyde", Angew. Chem. Int. Ed. 2008, 47, 2082-2084.
Boeckman et al., "Direct Enantioselective Organocatalytic Hydroxymethylation of Qldehydes Catalyzed by a, a-Diphenylprolinol Trimethylsilyl Ether", Org. Lett., vol. 11, No. 20, 2009, 4544-4547.
Kano et al., "syn-Selective and Enantioselective Direct Cross-Aldol Reactions between Aldehydes Catalyzed by an Axially Chiral Amino Sulfonamide", Angew. Chem. Int. Ed. 2007, 46, 1738-1740.
Kano et al., "A Designer Axially Chiral Amino Sulfonamide as an Efficient Organocatalyst for Direct Asymmetric anti-Selective Mannich Reactions and syn-Selective Cross-Aldol Reactions", Chem. Eur. J., 2009, 15, 6678-6687.
Kano et al., "Efficient Organocatalytic Cross-Aldo Reaction between Aliphatic Aldehydes through Their Functional Differentiation", J. Am. Chem. Soc., 2011, 133, 18130-18133.
Marked et al., "Asymmetric Histidine-Catalyzed Cross-Aldol Reactions of Enolizable Aldehydes: Access to defined configured Quaternary Stereogenic Centers", J. Am. Chem. Soc., 2009, 131, 16642-16643.
Li et al., "Chiral Primary—Tertiary Diamine—Bronsted Acid Salt Catalyzed Syn-Selective Cross-Aldol Reaction of Aldehydes", J. Org. Chem., 2010, 75, 4501-4507.
Denmark et al.,"The First Catalytic, Diastereoselectie, and Enantioselective Crossed-Aldol Reactions of Aldehydes", Angew. Chem. Int. Ed., 2001, 40, No. 24, 47594762.
Denmark et al., "Chiral phosphoramide-catalyzed, enantioselective, directed cross-aldol reactions of aldehydees", PNAS, Apr. 13, 2004, vol. 101, No. 15, 5439-5444.
Denmark et al., "Lewis Base Catalyzed Enantioselctive Aldol Addition of Acetaldehyde-Derived Silyl Enol Ether to Aldehydes", J. Org. Chem, 2005, 70, 10190-10193.
International Preliminary Report on Pattentability issued on Apr. 6, 2017, International Application No. PCT/JP2015/074733 (14 pages).

*Primary Examiner* — Sudhakar Katakam
*Assistant Examiner* — Jennifer C Sawyer
(74) *Attorney, Agent, or Firm* — Mintz Levin Cohn Ferris Glovsky and Popeo, P.C.; Peter F. Corless

(57) ABSTRACT

Provided is a process for producing an optically active hydroxyaldehyde or aminohydroxyaldehyde. The process for producing an optically active hydroxyaldehyde or aminohydroxyaldehyde is characterized by reacting an aldehyde or an imine with a boric acid enol ester in the presence of a copper compound and an optically active bidentate phosphine compound.

8 Claims, No Drawings

PROCESS FOR PRODUCING ALCOHOL ANALOGUE

CROSS-REFERENCE TO RELATED APPLICATIONS

This application is a National Phase application filed under 35 USC 371 of PCT International application No. PCT/JP/2015/074733 with an International Filing Date of Aug. 31, 2015, which claims under 35 U.S.C. § 119(a) the benefit of Japanese Application No. 2014-196358, filed Sep. 26, 2014, the entire contents of which are incorporated herein by reference.

TECHNICAL FIELD

The present invention relates to a method for producing optically active compounds using a borate enol ester with a copper compound and an optically active bidentate phosphine compound as catalytic components.

BACKGROUND ART

Asymmetric aldol reactions are a useful method for synthesizing optically active β-hydroxycarbonyl compounds. Among these, optically active β-hydroxyaldehydes have particularly high importance as intermediates of medicine, agricultural chemicals, perfume and the like. However, because the well known asymmetric aldol reactions use an enolate or an enolate equivalent prepared from a ketone or carboxylic acid derivative, a multistep process via an optically active β-hydroxycarboxylic acid derivative has been required to obtain an optically active β-hydroxyaldehyde. In order to efficiently obtain an optically active β-hydroxyaldehyde by fewer processes, an asymmetric aldol reaction using an enolate derived from an aldehyde or an enolate equivalent such as enamine is preferred. In addition, in order to selectively carry out asymmetric cross-aldol reactions with different aldehydes, a technique to achieve control of one aldehyde as an enolate or an enolate equivalent and another aldehyde as an electrophile is required. As asymmetric catalysts to synthesize optically active β-hydroxyaldehydes by asymmetric cross-aldol reactions between different aldehydes, which have been known until now, only some organocatalysts are known.

Specifically, there are a technique using a proline catalyst by MacMillan et al. (Non Patent Documents 1 and 2), Barbas et al. (Non Patent Document 3), and Cordova et al. (Non Patent Document 4), a technique using an imidazolidinone catalyst by MacMillan et al. (Non Patent Document 5), a technique using a prolinol catalyst by Hayashi et al. (Non Patent Document 6), and Boeckman et al. (Non Patent Document 7), a technique using an axially chiral organocatalyst by Maruoka et al. (Non Patent Documents 8, 9 and 10), a technique using a histidine catalyst by Mahrwald et al. (Non Patent Document 11), and a technique using a diamine catalyst by Luo et al. (Non Patent Document 12) and the like. As a technique to achieve combinations of an electrophile aldehyde and a nucleophile aldehyde in asymmetric cross-aldol reactions as desired, a technique of Denmark et al. using an optically active Lewis base organocatalyst and a silyl enol ether derived from an aldehyde (Non Patent Documents 13, 14 and 15) is known.

CITATION LIST

Non Patent Document

Non Patent Document 1: J. Am. Chem. Soc. 2002, 124, 6798
Non Patent Document 2: Science 2004, 305, 1752
Non Patent Document 3: Tetrahedron Lett. 2002, 43, 9591
Non Patent Document 4: Chem. Eur. J. 2005, 11, 4772
Non Patent Document 5: Angew. Chem. Int. Ed. 2004, 43, 6722
Non Patent Document 6: Angew. Chem. Int. Ed. 2008, 47, 2082
Non Patent Document 7: Org. Lett. 2009, 11, 4544
Non Patent Document 8: Angew. Chem. Int. Ed. 2007, 46, 1738
Non Patent Document 9: Chem. Eur. J. 2009, 15, 6678
Non Patent Document 10: J. Am. Chem. Soc. 2011, 133, 18130
Non Patent Document 11: J. Am. Chem. Soc. 2009, 131, 16642
Non Patent Document 12: J. Org. Chem. 2010, 75, 4501
Non Patent Document 13: Angew. Chem. Int. Ed. 2001, 40, 4759
Non Patent Document 14: Proc. Natl. Acad. Sci. USA 2004, 101, 5439
Non Patent Document 15: J. Org. Chem. 2005, 70, 10190

SUMMARY OF THE INVENTION

Problems to be Solved by the Invention

In the conventional techniques, it has been difficult to achieve high enantioselectivity and wide substrate versatility, and further to control chemical selectivity regardless of substrates used. That is, in the conventional techniques using an organocatalyst, chemical selectivity dependent on only the steric and electronic factors of aldehydes or imines is achieved, and thus a means for combining an electrophile and a nucleophile has been significantly restricted. Specifically, the substrate versatility has been poor, and thus, for example, it has been impossible to use a sterically small straight-chain aldehyde such as propanal as an electrophile. In addition, in the technique using a silyl enol ether as an aldehyde enolate equivalent, there have remained problems in that for example enantioselectivity is moderate and substrate versatility is poor. In addition, there have not existed a technique to achieve a catalytic asymmetric reaction using a readily available borate enol ester as an aldehyde enolate equivalent, and a technique to use a highly reactive asymmetric metal catalyst.

Means for Solving the Problems

As a result of intensive studies to solve the above problems, the present inventors consequently found that a borate enol ester obtained by isomerizing an allyl borate, which is readily available at a low cost, was reacted with an aldehyde in the presence of a copper compound and an optically active bidentate phosphine compound to obtain an optically active hydroxyaldehyde with high enantioselectivity and diastereoselectivity, and also found that the produced aldehyde could be led to a polyol by repeating the same reaction, and an aminohydroxyaldehyde could be obtained by using an imine in place of an aldehyde, thereby completing the present invention.

That is, the present invention relates to a method for producing a compound represented by the following general formula (3),

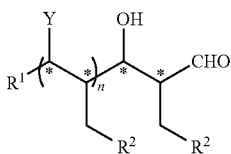

(wherein, $R^1$ represents an optionally substituted hydrocarbon group, or an optionally substituted heterocyclic group. $R^2$ represents a hydrogen atom or a $C_{1-6}$ alkyl group. Y represents a hydroxy group or NHX (X represents an optionally substituted thiophosphinoyl group.). n represents 0 or 1. * represents an asymmetric carbon atom.)

by reacting a borate enol ester represented by the following general formula (2):

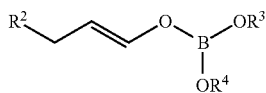

(wherein, $R^2$ represents a hydrogen atom or a $C_{1-6}$ alkyl group. $R^3$ and $R^4$ represent a $C_{1-4}$ alkyl group, or $R^3$ and $R^4$ optionally together form a methylene chain which is optionally substituted with alkyl group(s).)

and a compound represented by the following formula (1):

$$R^1CH=Z \qquad (1)$$

(wherein, $R^1$ represents an optionally substituted hydrocarbon group or an optionally substituted heterocyclic group. Z represents an oxygen atom or NX (X represents an optionally substituted thiophosphinoyl group.))

in the presence of a copper compound and an optically active bidentate phosphine compound.

Effects of the Invention

According to the present invention, optically active hydroxyaldehydes or aminohydroxyaldehydes can be produced with high enantioselectivity and diastereoselectivity at a high yield.

The present invention can also use a sterically small straight-chain aldehyde such as propanal as an electrophile, and has excellent substrate versatility, and thus not only many electrophilic aldehyde compounds such as aliphatic aldehydes, aromatic aldehydes, araliphatic aldehydes and heterocyclic aldehydes and derivatives thereof can be used as a substrate, but also imine (—CH=N—R) compounds corresponding to these aldehyde compounds can be used as a substrate.

Further, according to the present invention, the produced aldehyde can be led to a polyol by repeating the same reaction.

Borate enol esters used as carbonyl enolate equivalents such as aldehyde enolate equivalents in the method of the present invention can be readily obtained at a low cost by isomerizing allyl borates, and are thus readily available.

DESCRIPTION OF EMBODIMENTS

The method of the present invention relates to an asymmetric aldol reaction which is carried out in the presence of an optically active bidentate phosphine compound and uses a borate enol ester as a carbonyl enolate equivalent such as an aldehyde enolate equivalent. More specifically, the method of the present invention relates to an asymmetric aldol reaction in which a borate enol ester is reacted with an aldehyde compound or an imine compound corresponding thereto in the presence of a copper compound and an optically active bidentate phosphine compound.

The method of the present invention is not limited to an asymmetric aldol reaction by an aldehyde compound and an aldehyde compound, and should be interpreted as a method in which a borate enol ester as a nucleophile is reacted with an electrophilic substrate having for example a carbonyl group and an imino group in the presence of a copper compound and an optically active bidentate phosphine compound to produce a product by a nucleophilic reaction.

The aspect of the present invention will be described in more detail as follows.

(1) A method for producing a compound represented by the following general formula (3),

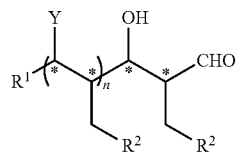

(wherein, $R^1$ represents an optionally substituted hydrocarbon group, or an optionally substituted heterocyclic group. $R^2$ represents a hydrogen atom or a $C_{1-6}$ alkyl group. Y represents a hydroxy group or NHX (X represents an optionally substituted thiophosphinoyl group.). n represents 0 or 1. * represents an asymmetric carbon atom.)

by reacting an aldehyde compound or an imine compound corresponding thereto represented by the following general formula (1):

$$R^1CH=Z \qquad (1)$$

(wherein, $R^1$ represents an optionally substituted hydrocarbon group, or an optionally substituted heterocyclic group. Z represents an oxygen atom or NX (X represents an optionally substituted thiophosphinoyl group.))

is reacted with a borate enol ester represented by the following general formula (2):

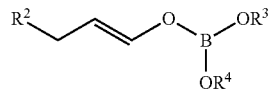

(wherein $R^2$ represents a hydrogen atom or a $C_{1-6}$ alkyl group. $R^3$ and $R^4$ represent a $C_{1-4}$ alkyl group, or $R^3$ and $R^4$ may together form a methylene chain which may be substituted with alkyl group(s).)

in the presence of a copper compound and an optically active bidentate phosphine compound.

(2) The method according to (1) above, wherein the reaction is carried out further in the presence of an additive.

(3) The method according to (2) above, wherein the additive is a compound selected from the group consisting of triethylamine, triphenylphosphine oxide, tributylphosphine oxide and hexamethyltriphosphoramide.

(4) The method according to any one of (1) to (3) above, wherein n in the general formula (3) is 0.

(5) The method according to any one of (1) to (3) above, wherein n in the general formula (3) is 1.

(6) The method according to (5) above, characterized in that a reaction product produced by the method according to any one of (1) to (3) above is further reacted with a borate enol ester represented by the general formula (2).

(7) The method according to any one of (1) to (6) above, wherein the optically active bidentate phosphine compound is an optically active bidentate phosphine compound having axial chirality.

(8) The method according to any one of (1) to (7) above, wherein the optically active bidentate phosphine compound is a phosphine compound represented by the following general formula (4):

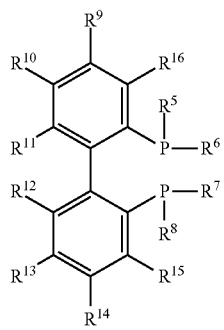

(4)

(wherein, in the formula (4), $R^5$, $R^6$, $R^7$ and $R^8$ each independently represent a phenyl group, a cyclopentyl group or a cyclohexyl group which may be substituted with substituent(s) selected from the group consisting of an alkyl group, an alkoxy group and a halogen atom. $R^9$, $R^{10}$, $R^{11}$, $R^{12}$, $R^{13}$, $R^{14}$, $R^{15}$ and $R^{16}$ may be the same or different from one another, and each represents a hydrogen atom, an optionally substituted alkyl group, an alkoxy group, an acyloxy group, a halogen atom, a haloalkyl group or a dialkylamino group, or $R^{10}$ and $R^{11}$, and $R^{12}$ and $R^{13}$ may together form an optionally substituted methylene chain or an optionally substituted alkylenedioxy group, with the proviso that $R^{11}$ and $R^{12}$ are not a hydrogen atom.)

(9) The method according to any one of (1) to (8) above, characterized in that a borate enol ester represented by the general formula (2) is produced by the isomerization reaction of the following scheme using an iridium catalyst:

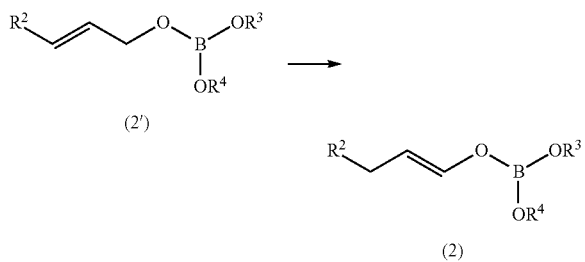

(wherein, in the scheme, $R^2$ represents a hydrogen atom or a $C_{1-6}$ alkyl group. $R^3$ and $R^4$ represent a $C_{1-4}$ alkyl group, or $R^3$ and $R^4$ may together form a methylene chain which may be substituted with alkyl group(s).)

The present invention will now be described in detail.

In an aldehyde compound represented by the general formula (1) in the production method of the present invention, the hydrocarbon group represented by $R^1$ is a monovalent group consisting of carbon atoms and hydrogen atoms, and examples thereof include an alkyl group, an alkenyl group, an alkynyl group, an aryl group, an aralkyl group and the like.

In a compound represented by the general formula (1), the alkyl group as one of the hydrocarbon group represented by $R^1$ maybe straight-chain, branched-chain, or cyclic. Examples of the alkyl group include $C_{1-15}$, preferably $C_{1-10}$, and more preferably $C_{1-6}$ alkyl groups, and specific examples thereof include a methyl group, an ethyl group, a n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group, a cyclopropyl group, a cyclobutyl group, a cyclopentyl group, a cyclohexyl group and the like.

In addition, these alkyl groups may have substituent(s), and the substituents include a hydrocarbon group, an aliphatic heterocyclic group, an aromatic heterocyclic group, an alkoxy group, an alkylenedioxy group, an aryloxy group, an aralkyloxy group, a heteroaryloxy group, a substituted amino group and a halogen atom and the like.

Examples of the hydrocarbon group as a substituent of the alkyl group include an alkyl group, an alkenyl group, an alkynyl group, an aryl group, an aralkyl group and the like.

The alkyl group may be straight-chain, branched-chain or cyclic. Examples thereof include $C_{1-15}$, preferably $C_{1-10}$, more preferably $C_{1-6}$ alkyl groups, and specific examples thereof include a methyl group, an ethyl group, an n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group, a cyclopropyl group, a cyclobutyl group, a cyclopentyl group, a cyclohexyl group and the like.

The alkenyl group may be straight-chain or branched-chain. Examples thereof include $C_{2-15}$, preferably $C_{2-10}$, more preferably $C_{2-6}$ alkenyl groups, and specific examples thereof include a vinyl group, a propenyl group, a 1-butenyl group, a pentenyl group, a hexenyl group and the like.

The alkynyl group may be straight-chain or branched-chain. Examples thereof include $C_{2-15}$, preferably $C_{2-10}$, more preferably $C_{2-6}$ alkynyl groups, and specific examples thereof include an ethynyl group, a 1-propynyl group, a 2-propynyl group, a 1-butynyl group, a 3-butynyl group, a pentynyl group, a hexynyl group and the like.

Examples of the aryl group include $C_{6-14}$ aryl groups, and specific examples thereof include a phenyl group, a naphthyl group, an anthryl group, a phenanthryl group, a biphenyl group and the like.

The aralkyl group is a group in which at least one hydrogen atom of an alkyl group is substituted with said aryl group. Examples thereof include preferably $C_{7-12}$ aralkyl groups, and specific examples thereof include a benzyl group, a 2-phenylethyl group, a 1-phenylpropyl group, a 3-naphthylpropyl group and the like.

Examples of the aliphatic heterocyclic group as a substituent of said alkyl group include 5 to 8-membered, preferably 5 or 6-membered monocyclic aliphatic heterocyclic groups and polycyclic or condensed ring aliphatic heterocyclic groups which have 2 to 14 carbon atoms and contain at least one, preferably 1 to 3 heteroatoms such as a nitrogen atom, an oxygen atom and a sulfur atom as heteroatoms. Specific examples of the aliphatic heterocyclic group include, for example, a 2-oxopyrrolidino group, a piperidino group, a piperazinyl group, a morpholino group, a tetrahydrofuryl group, a tetrahydropyranyl group, a tetrahydrothienyl group and the like.

Examples of the aromatic heterocyclic group as a substituent of said alkyl group include 5 to 8-membered, preferably 5 or 6-membered monocyclic heteroaryl groups and polycyclic or condensed ring heteroaryl groups which have 2 to 15 carbon atoms and contain at least one, preferably 1 to 3 heteroatoms such as a nitrogen atom, an oxygen atom and a sulfur atom as heteroatoms, and specific examples thereof include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzimidazolyl group, a benzoxazolyl group, a benzothiazolyl group and the like.

The alkoxy group as a substituent of said alkyl group may be straight-chain, branched-chain or cyclic. Examples thereof include $C_{1-6}$ alkoxy groups, and specific examples thereof include a methoxy group, an ethoxy group, an n-propoxy group, an isopropoxy group, an n-butoxy group, a 2-butoxy group, an isobutoxy group, a tert-butoxy group, an n-pentyloxy group, a 2-methylbutoxy group, a 3-methylbutoxy group, a 2,2-dimethylpropyloxy group, an n-hexyloxy group, a 2-methylpentyloxy group, a 3-methylpentyloxy group, a 4-methylpentyloxy group, a 5-methylpentyloxy group, a cyclohexyloxy group and the like.

Examples of the alkylenedioxy group as a substituent of said alkyl group include $C_{1-3}$ alkylenedioxy groups, and specific examples thereof include a methylenedioxy group, an ethylenedioxy group, a propylenedioxy group, an isopropylidenedioxy group and the like.

Examples of the aryloxy group as a substituent of said alkyl group include $C_{6-14}$ aryloxy groups, and specific examples thereof include a phenyloxy group, a naphthyloxy group, an anthryloxy group and the like.

Examples of the aralkyloxy group as a substituent of said alkyl group include $C_{7-12}$ aralkyloxy groups, and specific examples thereof include a benzyloxy group, a 2-phenylethoxy group, a 1-phenylpropoxy group, a 2-phenylpropoxy group, a 3-phenylpropoxy group, a 1-phenylbutoxy group, a 2-phenylbutoxy group, a 3-phenylbutoxy group, a 4-phenylbutoxy group, a 1-phenylpentyloxy group, a 2-phenylpentyloxy group, a 3-phenylpentyloxy group, a 4-phenylpentyloxy group, a 5-phenylpentyloxy group, a 1-phenylhexyloxy group, a 2-phenylhexyloxy group, a 3-phenylhexyloxy group, a 4-phenylhexyloxy group, a 5-phenylhexyloxy group, a 6-phenylhexyloxy group and the like.

Examples of the heteroaryloxy group as a substituent of said alkyl group include heteroaryloxy groups which have 2 to 14 carbon atoms and contain at least one, preferably 1 to 3 heteroatoms such as a nitrogen atom, an oxygen atom and a sulfur atom as heteroatoms, and specific examples thereof include a 2-pyridyloxy group, a 2-pyrazyloxy group, a 2-pyrimidyloxy group, a 2-quinolyloxy group and the like.

The substituted amino groups as a substituent of said alkyl group include an amino group in which one or two hydrogen atoms of the amino group are substituted with substituents such as an alkyl group, an aryl group, and an aralkyl group.

Specific examples of amino groups substituted with alkyl group(s), i.e. alkyl group-substituted amino groups include mono or dialkylamino groups such as an N-methylamino group, an N,N-dimethylamino group, an N,N-diethylamino group, an N,N-diisopropylamino group, and an N-cyclohexylamino group.

Specific examples of amino groups substituted with aryl group(s), i.e. aryl group-substituted amino groups include mono or diarylamino groups such as an N-phenylamino group, an N,N-diphenylamino group, an N-naphthylamino group, and an N-naphthyl-N-phenylamino group.

Specific examples of amino groups substituted with aralkyl group(s), i.e. aralkyl group-substituted amino groups include mono or diaralkylamino groups such as an N-benzylamino group, an N,N-dibenzylamino group and the like.

The halogen atoms as a substituent of said alkyl group include a fluorine atom, a chlorine atom, a bromine atom and an iodine atom.

Among these substituents, a hydrocarbon group, an aliphatic heterocyclic group, an aromatic heterocyclic group, an alkoxy group, an alkylenedioxy group, an aryloxy group, an aralkyloxy group, a heteroaryloxy group or a substituted amino group can be further substituted with groups selected from the substituent group given above.

In a compound represented by the general formula (1), one of the hydrocarbon group represented by $R^1$ is an alkenyl group which may be straight- or branched-chain or cyclic and has 2 to 20 carbon atoms, and preferably 2 to 10 carbon atoms. Specific alkenyl groups include a vinyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-cyclopentenyl group, a 3-cyclopentenyl group, a 1-hexenyl group, a 2-hexenyl group, a 3-hexenyl group, a 4-hexenyl group, a 5-hexenyl group, a 1-cyclohexenyl group, and a 3-cyclohexenyl group and the like.

In addition, these alkenyl groups may have substituent(s), and the substituent(s) include an alkyl group, a halogen atom, an aryl group and a heterocyclic group and the like, and specific examples thereof include those as mentioned above.

In a compound represented by the general formula (1), one of the hydrocarbon group represented by $R^1$ is an alkynyl group which may be straight- or branched-chain, and specific examples thereof include an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group and a 5-hexynyl group and the like.

These alkynyl groups may have substituent(s), and the substituent(s) include an alkyl group, an aryl group, a heterocyclic group and a trialkylsilyl group and the like, and specific examples of the alkyl group, the aryl group and the heterocyclic group include those as mentioned above.

In a compound represented by the general formula (1), one of the hydrocarbon group represented by $R^1$ is an aryl group, and specific examples thereof include aryl groups as mentioned above. These aryl groups may have substituent(s), and the substituent(s) include an alkyl group, an aryl group, a heterocyclic group and the like, and specific examples thereof include those as mentioned above.

In a compound represented by the general formula (1), the heterocyclic group represented by $R^1$ includes an aliphatic or aromatic heterocyclic group, and specific examples thereof include heterocyclic groups as mentioned above. These heterocyclic groups may have substituent(s), and the substituent(s) include an alkyl group, an aryl group, a heterocyclic group and the like, and specific examples thereof include those as mentioned above.

In a compound represented by the general formula (1), the thiophosphinoyl group represented by X of the NX group includes a group represented by the general formula —P(S)$Q^1Q^2$ (wherein, $Q^1$ and $Q^2$ each independently represent a $C_{1-10}$ alkyl group, or a $C_{6-12}$ monocyclic, polycyclic or condensed ring aryl group which maybe substituted with substituent(s) selected from the group consisting of an alkyl group, a haloalkyl group, an alkoxy group, a halogen atom and an alkylenedioxy group.) Herein, the alkyl group and the aryl group and the like include those as mentioned above.

In borate enol esters represented by the general formula (2) in the present invention, examples of the $C_{1-6}$ alkyl group represented by $R^2$ include a methyl group, an ethyl group, an n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group and the like, and a methyl group is preferred. The alkyl group represented by $R^3$ and $R^4$ is preferably a $C_{1-4}$ alkyl group, and specific examples thereof include a methyl group, an ethyl group, an n-propyl group, an isopropyl group, an n-butyl group, a 2-butyl group, an isobutyl group, a tert-butyl group and the like.

Examples of the methylene chain formed by $R^3$ and $R^4$ include a methylene group, an ethylene group, a trimethylene group and the like, and alkyl group (s) as a substituent of these methylene chains include preferably a $C_{1-6}$ alkyl group, and examples thereof include a methyl group, an ethyl group and the like.

In the production method of the present invention, as a compound represented by the general formula (1) and a borate enol ester represented by the general formula (2) which are used as raw materials, commercially available products can be directly used or those prepared by a known method can be used. Examples of known preparation methods include a method in which a double bond is isomerized using an iridium catalyst as described in Documents (e.g. Chem. Commun., 1998, 1337 and Organometallics, 1999, 18, 413) and the like.

The copper compounds and optically active bidentate phosphine compounds used as catalytic components in the present invention will now be described.

Examples of the copper compound include CuAr (Ar represents an aryl group), CuR (R represents an alkyl group), CuX (X represents a halogen group), CuOR (OR represents an alkoxy group and a phenoxy group), and $CuO_2CR$ ($O_2CR$ represents a group in which the hydrogen atom is removed from a carboxylic acid), and CuAr (Ar represents an aryl group) and the like are preferred. Herein, the alkyl group and the aryl group and the like include those as mentioned above. Herein, Ar and R may have substituent(s), and the substituent(s) include an alkyl group, an alkoxy group, a halogen group and the like.

Specific copper compounds include mesitylcopper, copper fluoride, copper iodide, tert-butoxy copper, copper acetate and the like, and mesitylcopper is preferred. A copper compound or a precursor thereof and a compound which reacts with said copper compound or said precursor thereof are allowed to coexist in a reaction system, thereby being able to obtain a new copper compound in the reaction system.

Next, the optically active bidentate phosphine compounds used in the present invention will be described.

The bidentate phosphine compounds used in the present invention are preferably those having an axially chiral structure, and one of them is a compound having an axially chiral structure represented by the following general formula (4):

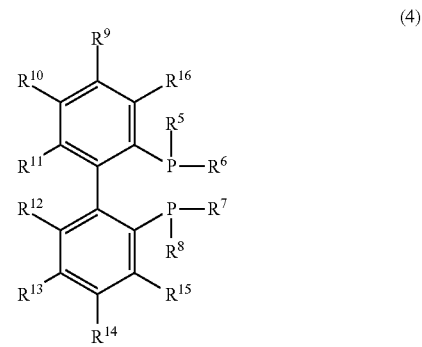

(4)

(wherein, in the formula (4), $R^5$, $R^6$, $R^7$ and $R^8$ each independently represent a phenyl group, a cyclopentyl group or a cyclohexyl group which may be substituted with substituent(s) selected from the group consisting of an alkyl group, an alkoxy group and a halogen atom. $R^9$, $R^{10}$, $R^{11}$, $R^{12}$, $R^{13}$, $R^{14}$, $R^{15}$ and $R^{16}$ may be the same or different from one another, and each represents a hydrogen atom, an optionally substituted alkyl group, an alkoxy group, an acyloxy group, a halogen atom, a haloalkyl group or a dialkylamino group, or $R^{10}$ and $R^{11}$, and $R^{12}$ and $R^{13}$ may together form an optionally substituted methylene chain or an optionally substituted alkylenedioxy group, with the proviso that $R^{11}$ and $R^{12}$ are not a hydrogen atom.)

As substituents of $R^5$, $R^6$, $R^7$ and $R^8$, examples of the alkyl group include $C_{1-6}$ alkyl groups which may be straight- or branched-chain such as a methyl group and a tert-butyl group, and examples of the alkoxy group include $C_{1-6}$ alkoxy groups which may be straight- or branched-chain such as a methoxy group and a tert-butoxy group, and examples of the halogen atom include a chlorine atom, a bromine atom, a fluorine atom and the like, and a plurality positions on a phenyl ring and a cycloalkyl ring may be substituted with these substituents.

Specific $R^5$, $R^6$, $R^7$ and $R^8$ include a phenyl group, a p-tolyl group, a m-tolyl group, an o-tolyl group, a 3,5-xylyl group, a 3,5-di-tert-butylphenyl group, a p-tert-butylphenyl group, a p-methoxyphenyl group, a 3,5-di-tert-butyl-4-methoxyphenyl group, a p-chlorophenyl group, a m-fluorophenyl group, a cyclopentyl group and a cyclohexyl group and the like.

In $R^9$ to $R^{16}$, examples of the alkyl group include $C_{1-6}$ alkyl groups which may be straight- or branched-chain such as a methyl group and a tert-butyl group, and examples of the alkoxy group include $C_{1-6}$ alkoxy groups which may be straight- or branched-chain such as a methoxy group and a tert-butoxy group, and examples of the acyloxy group include an acetoxy group, a propanoyloxy group, a trifluoroacetoxy group, and a benzoyloxy group and the like, and examples of the halogen atom include a chlorine atom, a bromine atom, a fluorine atom and the like, and examples of the haloalkyl group include $C_{1-4}$ haloalkyl groups such as a trifluoromethyl group, and examples of the dialkylamino group include a dimethylamino group, a diethylamino group or the like.

The optionally substituted methylene chain and the optionally substituted alkylenedioxy group formed by $R^{10}$ and $R^{11}$, and $R^{12}$ and $R^{13}$ are preferably a $C_{1-4}$ methylene chain, a methylenedioxy group and an ethylenedioxy group, and specific examples of the methylene chain include a methylene group, an ethylene group, a trimethylene group and a tetramethylene group. Substituents of the methylene chain and the alkylenedioxy group include an alkyl group and a halogen atom and the like, and specific examples thereof include $C_{1-4}$ alkyl groups as mentioned above and a fluorine atom and the like.

Specific examples of the optically active phosphine represented by the above general formula (4) include, for example,
2,2'-bis(diphenylphosphino)-5,5',6,6',7,7',8,8'-octahydro-1, 1'-binaphthyl,
2,2'-bis(di-p-tolylphosphino)-5,5',6,6',7,7',8,8'-octahydro-1, 1'-binaphthyl,
2,2'-bis(di-m-tolylphosphino)-5,5',6,6',7,7',8,8'-octahydro-1,1'-binaphthyl,
2,2'-bis(di-3,5-xylylphosphino)-5,5',6,6',7,7',8,8'-octahydro-1,1'-binaphthyl,
2,2'-bis(di-p-tertiary-butylphenylphosphino)-5,5',6,6',7,7',8, 8'-octahydro-1,1'-binaphthyl,
2,2'-bis(di-p-methoxyphenylphosphino)-5,5',6,6',7,7',8,8'-octahydro-1,1'-binaphthyl,
2,2'-bis(di-p-chlorophenylphosphino)-5,5',6,6',7,7',8,8'-octahydro-1,1'-binaphthyl,
2,2'-bis(dicyclopentylphosphino)-5,5',6,6',7,7',8,8'-octahydro-1,1'-binaphthyl,
2,2'-bis(dicyclohexylphosphino)-5,5',6,6',7,7',8,8'-octahydro-1,1'-binaphthyl,
((4,4'-bi-1,3-benzodioxole)-5,5'-diyl)bis(diphenylphosphine),
(4,4'-bi-1,3-benzodioxole)-5,5'-diyl)bis(bis(3,5-dimethylphenyl)phosphine),
((4,4'-bi-1,3-benzodioxole)-5,5'-diyl)bis(bis(3,5-di-t-butyl-4-methoxyphenyl)phosphine) (hereinafter referred to as DTBM-segphos),
((4,4'-bi-1,3-benzodioxole)-5,5'-diyl)bis(bis(4-methoxyphenyl)phosphine),
((4,4'-bi-1,3-benzodioxole)-5,5'-diyl)bis(dicyclohexylphosphine),
((4,4'-bi-1,3-benzodioxole)-5,5'-diyl)bis(bis(3,5-di-t-butylphenyl)phosphine),
2,2'-bis(diphenylphosphino)-4,4',6,6'-tetramethyl-5,5'-dimethoxy-1,1'-biphenyl,
2,2'-bis(di-p-methoxyphenylphosphino)-4,4',6,6'-tetramethyl-5,5'-dimethoxy-1,1'-biphenyl,
2,2'-bis(diphenylphosphino)-4,4',6,6'-tetra(trifluoromethyl)-5,5'-dimethyl-1,1'-biphenyl,
2,2'-bis(diphenylphosphino)-4,6-di(trifluoromethyl)-4',6'-dimethyl-5'-methoxy-1,1'-biphenyl,
2-dicyclohexylphosphino-2'-diphenylphosphino-4,4',6,6'-tetramethyl-5,5'-dimethoxy-1,1'-biphenyl,
2,2'-bis(diphenylphosphino)-6,6'-dimethyl-1,1-biphenyl,
2,2'-bis(diphenylphosphino)-4,4',6,6'-tetramethyl-1,1'-biphenyl,
2,2'-bis(diphenylphosphino)-3,3',6,6'-tetramethyl-1,1'-biphenyl),
2,2'-bis(diphenylphosphino)-4,4'-difluoro-6,6'-dimethyl-1, 1'-biphenyl,
2,2'-bis(diphenylphosphino)-4,4'-bis(dimethylamino)-6,6'-dimethyl-1,1'-biphenyl,
2,2'-bis(di-p-tolylphosphino)-6,6'-dimethyl-1,1'-biphenyl,
2,2'-bis(di-o-tolylphosphino)-6,6'-dimethyl-1,1'-biphenyl,
2,2'-bis(di-m-fluorophenylphosphino)-6,6'-dimethyl-1,1'-biphenyl,
1,11-bis(diphenylphosphino)-5,7-dihydrobenzo[c,e]oxepin,
2,2'-bis(diphenylphosphino)-6,6'-dimethoxy-1,1'-biphenyl,
2,2'-bis(diphenylphosphino)-5,5',6,6'-tetramethoxy-1,1'-biphenyl,
2,2'-bis(di-p-tolylphosphino)-6,6'-dimethoxy-1,1'-biphenyl,
2,2'-bis(diphenylphosphino)-4,4',5,5',6,6'-hexamethoxy-1, 1'-biphenyl and the like, but are not limited thereto. Among these, DTBM-segphos is preferred.

In the production method of the present invention, a borate enol ester represented by the general formula (2), preferably a borate enol ester represented by the general formula (2) obtained by isomerizing the double bond of a borate ester represented by the general formula (2'), is added to a solution containing a copper compound and an optically active bidentate phosphine, catalytic components, and a compound represented by the general formula (1) is added thereto, and the obtained mixture is then stirred at an appropriate reaction temperature for appropriate reaction time, thereby being able to produce an optically active compound represented by the general formula (3), a target substance. Conversely, the catalytic components can be added to the reaction substrate.

At this time, as a borate enol ester of the general formula (2) added to a reaction system, one isolated after the isomerization reaction or a solution without isolation can be used, and one in the solution state is preferably used.

The amount of borate enol ester represented by the general formula (2) used with respect to a compound represented by the general formula (1) is 1 to 5-fold mols, preferably 1.1 to 2-fold mols, and more preferably 1.1 to 1.5-fold mols, which is sufficient.

The iridium catalysts used when preparing a borate enol ester represented by the general formula (2) by isomerization of a borate ester represented by the general formula (2') include
(1,5-cyclooctadiene)bis(methyldiphenylphosphine)iridium (I) hexafluorophosphate, or one in which
bis(1,5-cyclooctadiene)iridium(I) hexafluorophosphate and a trialkylphosphine are mixed in a reaction mixture, or the like, and preferably
(1,5-cyclooctadiene)bis(methyldiphenylphosphine)iridium (I) hexafluorophosphate, or a combination of
bis(1,5-cyclooctadiene)iridium(I) hexafluorophosphate and tributylphosphine. The amount of iridium catalyst used with respect to a borate ester represented by the general formula (2'), an isomerization substrate, can be 0.0001 to 0.5-fold mol, preferably 0.001 to 0.05-fold mol.

The isomerization reaction can be carried out in the presence of hydrogen gas in a reaction system.

The amount of copper compound and optically active bidentate phosphine, catalytic components, used with respect to a compound represented by the general formula (1) is 0.01 mol % to 50 mol %, preferably 1 mol % to 30 mol %, and more preferably 3 mol % to 10 mol %, which is sufficient.

Reaction solvents are not particularly limited as long as they do not interfere with the reactions, and examples thereof include amides such as N,N-dimethylformamide, N,N-diethylformamide, and N,N-dimethylacetamide; halogenated hydrocarbons such as dichloromethane, 1,2-dichloroethane, and o-dichlorobenzene; aliphatic hydrocarbons such as pentane, hexane, heptane, octane, decane, and cyclohexane; aromatic hydrocarbons such as toluene, and xylene; alcohols such as isopropanol, and tert-butanol; ethers such as diethyl ether, diisopropyl ether, tert-butyl methyl ether, dimethoxyethane, ethylene glycol diethyl ether, tetrahydrofuran, 1,4-dioxane, and 1,3-dioxolane; ketones such as acetone, 2-butanone, and cyclohexanone; sulfoxides such as dimethylsulfoxide and the like. Examples of more preferred solvents include tetrahydrofuran, acetone and isopropyl alcohol and the like. These solvents can be used alone or two or more solvents can be used appropriately in combination.

In the method of the present invention, a yield may be improved by adding additives in some cases. Additives used include triethylamine, triphenylphosphine oxide, tributylphosphine oxide, hexamethyltriphosphoramide and the like.

The reaction temperature naturally varies depending on substrates used, and the reaction can be carried out in a range of commonly −80° C. to 100° C., preferably −60° C. to 80° C., further preferably −80° C. to 80° C., and −80° C. to 20° C.

The reaction time naturally varies depending on substrates used, and is commonly for 10 minutes to 100 hours, preferably for 0.5 hours to 80 hours.

In the present reaction, conversion into an optically active polyol can be made by repeatedly reacting a borate enol ester represented by the general formula (2). That is, conversion into an optically active polyol can be made by continuing the reaction by further adding 1 to 5-fold mols, preferably 1.1 to 2-fold mols, and more preferably 1.1 to 1.5-fold mols of borate enol ester represented by the general formula (2) to the reaction system after the above reaction. Even when an aldehyde of the general formula (1) is replaced with an imine represented by the general formula (5), the reaction can be carried out in the same manner, thereby being able to obtain an aminoaldehyde.

X in a compound represented by the general formula (5) is preferably a thiophosphinyl group, and particularly preferably a diphenylthiophosphinyl group (Ph$_2$P(=S)).

The reaction mode is not particularly limited, and a batch method or a flow method can be used.

After completion of the reaction, a target optically active hydroxyaldehyde or aminohydroxyaldehyde can be obtained by using operation such as crystallization, distillation or each chromatography alone or using each operation in combination.

A corresponding diol can be obtained by reducing the obtained product with a hydrogenation agent such as sodium borohydride.

EXAMPLES

The present invention will now be described in more detail with reference to Examples, but it is not intended that the present invention is not limited thereto.

Example 1

Synthesis of Hydroxyaldehydes (1) Preparation of Borate Enolate

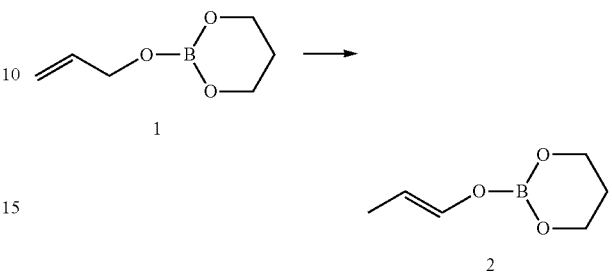

In a dry reaction glass container with argon atmosphere, (1,5-cyclooctadiene)bis (methyldiphenylphosphine) iridium (I) hexafluorophosphate (6.7 mg, 0.0079 mmol) and 1.6 mL of dehydrated acetone were added. Hydrogen gas was bubbled through the container at room temperature until the color of a reaction mixture was changed from red to colorless and transparent, and argon was bubbled again. This reaction mixture was cooled to 0° C., and allyl ester (223.6 μL, 1.575 mmol) was then added, and the obtained mixture was stirred at 0° C. for 30 minutes. With the temperature retained at 0° C., the solvent (acetone) was distilled off in vacuo, and the residue was cooled to −78° C., and 5.25 mL of THF was then added. The obtained mixture was used as a 0.3 M solution of borate enolate for the next aldol reaction.

(2) Aldol Reaction

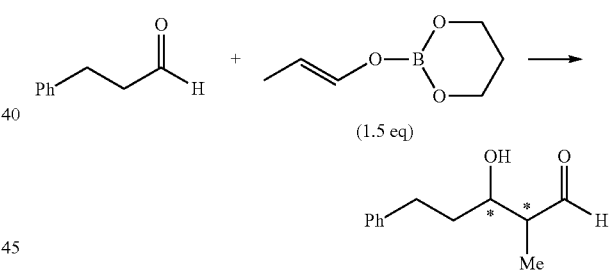

In a dried reaction container, triphenylphosphine oxide (27.8 mg, 0.10 mmol), mesitylcopper (0.9 mg, 0.005 mmol), (R)-DTBM-segphos (6.0 mg, 0.005 mmol), and 0.5 mL of THF were added, and the obtained mixture was cooled to −78° C. The 0.3 M solution of borate enolate obtained in (1) above (0.5 mL, 0.15 mmol), and hydrocinnamaldehyde (13.2 μL, 0.1 mmol) were sequentially added thereto, and the obtained mixture was stirred at −78° C. for 22 hours to obtain a hydroxyaldehyde.

Subsequently, the hydroxyaldehyde was derived to a diol to measure the yield and diastereoselectivity. To the reaction mixture, sodium borohydride (18.9 mg, 0.5 mmol) and 1 mL of methanol were added, and the temperature was gradually raised to room temperature. Water was added to the reaction mixture, and liquid-liquid extraction was carried out three times with diethyl ether. The combined organic layer was then washed with saturated solution of sodium chloride and dried with magnesium sulfate, and the solvent was distilled off. The obtained diol was isolated by silica gel column chromatography (hexane:ethyl acetate=1:1), and the yield was 95%. The enantioselectivity measured by HPLC (Daicel IA column, 254 nm, 1.0 mL/min, hexane:ethanol=60:1) was 99% ee (syn).

The retention time for the syn-form: 63.9 (minor) and 77.2 (major), the anti-form: 46.8 min and 49.0 min.

Example 2

Synthesis of Hydroxyaldehydes

In a dried reaction container, mesitylcopper (0.9 mg, 0.005 mmol), (R)-DTBM-segphos (6.0 mg, 0.005 mmol), 0.5 mL of THF and 7.7 µL of IPA were added, and the obtained mixture was cooled to −78° C. The 0.3 M solution of borate enolate (0.5 mL, 0.15 mmol) and hydrocinnamaldehyde (13.2 µL, 0.1 mmol) were sequentially added thereto, and the obtained mixture was stirred at −60° C. for 24 hours to obtain a hydroxyaldehyde.

Subsequently, the hydroxyaldehyde was derived to a diol in the same manner as in Example 1. The isolated yield was 93%, the diastereomeric ratio was 26:1 (syn:anti), and the enantioselectivity was 94% ee (syn).

Examples 3 to 12

Synthesis of Hydroxyaldehydes

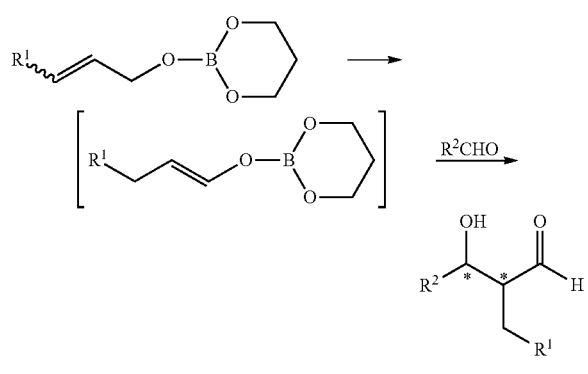

The reaction of the above scheme ($R^1$=H) was carried out in the same operation as in Example 2. The results are shown in Table 1.

TABLE 1

| Example | $R^2$ | Yield (%) | Diastereo-selectivity (syn:anti) | Syn-form Enantioselectivity (ee %) |
|---|---|---|---|---|
| 3 | n-Pentyl | 95 | >20:1 | 97.1 |
| 4 | 2-Methylpropyl | 80 | >20:1 | 97.3 |
| 5 | Cyclohexyl | 89 | >20:1 | 97.9 |
| 6 | Isopropyl | 87 | 15:1 | 94.9 |
| 7 | Phenyl | 75 | 12:1 | 96.3 |
| 8 | 4-Bromophenyl | 76 | 8:1 | 96.2 |
| 9 | Methyl | 82 | >20:1 | 96.1 |
| 10 | Ethyl | 70 | 16:1 | 95.0 |

The same operation as in Example 2 was carried out except that the borate enolate and aldehyde, both substrates, were changed. The results are shown in Table 2.

TABLE 2

| Example | $R^1$ | $R^2$ | Yield (%) | Diastereo-selectivity (syn:anti) | Syn-form Enantioselectivity (ee %) |
|---|---|---|---|---|---|
| 11 | Ethyl | Methyl | 80 | >20:1 | 97.0 |
| 12 | Phenyl | Methyl | 61 | 13:1 | 98.6 |

Example 13

Synthesis of Hydroxyaldehydes (1) Preparation of Borate Enolate

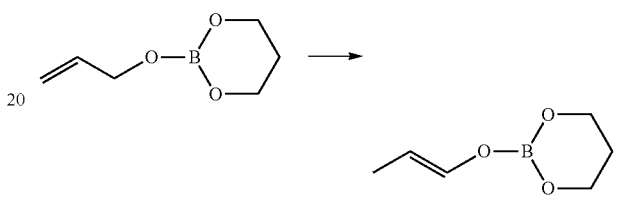

In a dry reaction glass container with argon atmosphere, bis (1,5-cyclooctadiene) iridium (I) hexafluorophosphate (4.4 mg, 0.0079 mmol), tributylphosphine (3.2 mg, 0.0158 mmol) and 1.6 mL of dehydrated acetone were added. Hydrogen gas was bubbled through the container at room temperature for 5 minutes, and argon was bubbled again. This reaction mixture was cooled to 0° C., and allyl ester (223.6 µL, 1.575 mmol) was then added, and the obtained mixture was stirred at 0° C. for 30 minutes. With the temperature retained at 0° C., the solvent (acetone) was distilled off in vacuo, and the residue was cooled to −78° C., and 5.25 mL of THF was then added. The obtained mixture was used as a 0.3 M solution of borate enolate for the next aldol reaction.

(2) Aldol Reaction

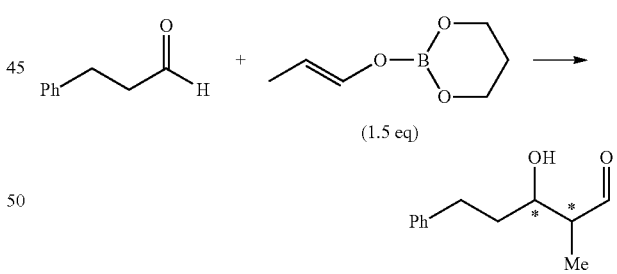

In a dried reaction container, mesitylcopper (0.9 mg, 0.005 mmol), (R)-DTBM-segphos (6.0 mg, 0.005 mmol), and 0.5 mL of THF were added, and the obtained mixture was cooled to −60° C. The 0.3 M solution of borate enolate obtained in (1) above (0.5 mL, 0.15 mmol), and hydrocinnamaldehyde (13.2 µL, 0.1 mmol) were sequentially added thereto, and the obtained mixture was stirred at −60° C. for 24 hours to obtain a hydroxyaldehyde.

The hydroxyaldehyde was derived to a diol in the same manner as in Example 1, and a yield and the like were measured. The isolated yield was 87%, the diastereomeric ratio was 8:1 (syn:anti), and the enantioselectivity was 87% ee (syn).

Example 14

Synthesis of β,δ-Dihydroxyaldehydes (1) Preparation of Borate Enolate

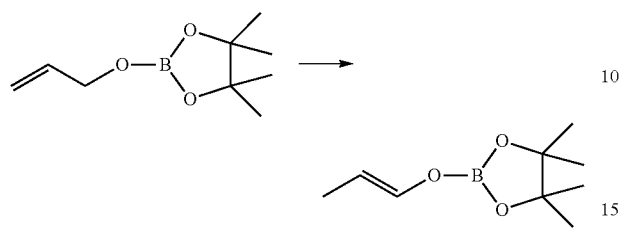

In a dry reaction glass container with argon atmosphere, (1,5-cyclooctadiene)bis(methyldiphenylphosphine)iridium (I) hexafluorophosphate (6.7 mg, 0.0079 mmol) and 1.6 mL of dehydrated acetone were added. Hydrogen gas was bubbled through the container at room temperature until the color of a reaction mixture was changed from red to colorless and transparent, and argon was bubbled again. This reaction mixture was cooled to 0° C., and allyl ester (340.2 µL, 1.575 mmol) was then added, and the obtained mixture was stirred at 0° C. for 30 minutes. With the temperature retained at 0° C., the solvent (acetone) was distilled off in vacuo, and the residue was cooled to −78° C., and 5.25 mL of THF was then added. The obtained mixture was used as a 0.3 M solution of borate enolate for the next aldol reaction.

(2) Successive Aldol Reactions

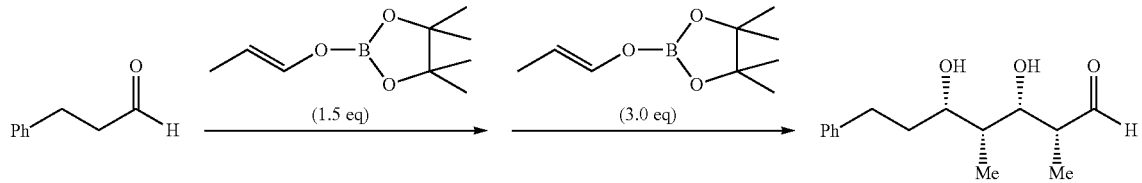

In a dry reaction glass container with argon atmosphere, mesitylcopper (0.9 mg, 0.005 mmol), (S)-DTBM-segphos (6.0 mg, 0.00505 mmol), isopropanol (7.7 µL, 0.1 mmol), and 0.25 mL of THF were added, and the obtained mixture was cooled to −78° C. The 0.3 M solution of borate enolate obtained in (1) above (0.5 mL, 0.15 mmol), and hydrocinnamaldehyde (13.2 µL, 0.1 mmol) were sequentially added thereto, and the obtained mixture was stirred at −60° C. for 24 hours.

Separately, mesitylcopper (0.9 mg, 0.005 mmol), (S)-DTBM-segphos (6.0 mg, 0.00505 mmol), isopropanol (0.39 µL, 0.005 mmol) and 0.25 mL of THF were added in a dry reaction glass container to prepare a catalytic solution (hereinafter, referred to as catalytic solution A). To the reaction mixture, the catalytic solution A (0.25 mL, 0.005 mmol), and a 0.4 M solution of borate enolate (0.25 mL, 0.1 mmol) were added, and the obtained mixture was stirred at −60° C. for 24 hours. Then, the catalytic solution A (0.25 mL, 0.005 mmol) and the 0.4 M solution of borate enolate (0.25 mL, 0.1 mmol) were further added, and the obtained mixture was stirred at −60° C. for 24 hours. Finally, the catalytic solution A (0.25 mL, 0.005 mmol) and the 0.4 M solution of borate enolate (0.25 mL, 0.1 mmol) were added, and the obtained mixture was stirred at −60° C. for 42 hours.

The obtained compound was derived to a triol, and a yield and diastereoselectivity were determined. To the reaction mixture, lithium borohydride (3 M THF solution, 0.33 mL, 1.0 mmol) was added, and the temperature was gradually raised to room temperature. To the reaction mixture, a 1 M aqueous solution of hydrochloric acid was added, and isolation was directly carried out by silica gel column chromatography (hexane:ethyl acetate=2:1 to 1:1). The yield and selectivity were measured by HPLC (Daicel IC column, 254 nm, 1.0 mL/min, acetonitrile:water=1:5), and the result was 72% (32:1:1 dr). The retention time for the syn, syn, syn-form: 16.1 (major) and 16.8 (minor), and the syn, anti, syn-form: 22.1 and 24.7. The enantioselectivity was 99% ee (syn, syn, syn).

Example 15

Synthesis of β,δ-Dihydroxyaldehydes

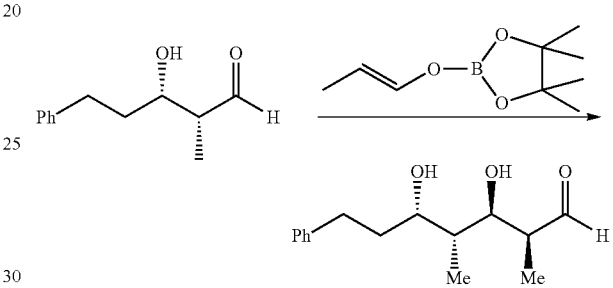

In a dry reaction glass container with argon atmosphere, mesitylcopper (0.7 mg, 0.0038 mmol), (R)-DTBM-segphos (4.5 mg, 0.0038 mmol), 4-methoxyphenol (0.9 mg, 0.0075 mmol), and 0.25 mL of THF were added, and the obtained mixture was cooled to −60° C. A 0.6 M solution of borate enolate (0.25 mL, 0.15 mmol), and a 0.3 M solution of (2R,3S)-3-hydroxy-2-methyl-5-phenylpentanal (0.25 mL, 0.075 mmol) were sequentially added thereto, and the obtained mixture was stirred at −60° C. for 40 hours.

The obtained compound was derived to a triol, and a yield and diastereoselectivity were determined. To the reaction mixture, lithium borohydride (3 M THF solution, 0.25 mL, 0.75 mmol) was added, and the temperature was gradually raised to room temperature. To the reaction mixture, a 1 M aqueous solution of hydrochloric acid was added, and isolation was directly carried out by silica gel column chromatography (hexane:ethyl acetate=2:1 to 1:1). The yield and selectivity were measured by HPLC (Daicel IC column, 254 nm, 1.0 mL/min, acetonitrile:water=1:5), and the result was 55% (28:1:1 dr). The retention time for the syn, anti, syn-form: 22.1 (major) and 24.7 (minor), and the syn, syn, syn-form: 16.1 and 16.8. The enantioselectivity was 99% ee (syn,anti,syn).

Example 16

Synthesis of δ-Amino-β-Hydroxyaldehydes

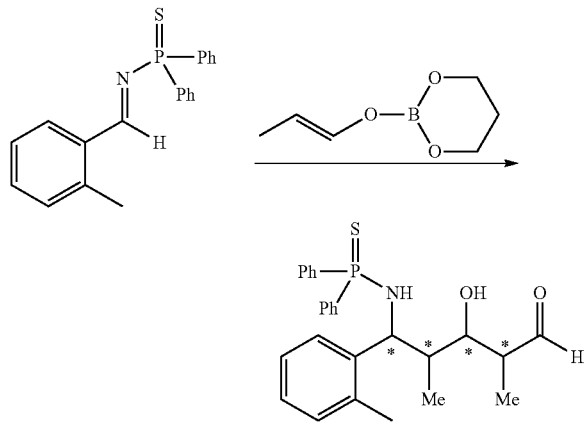

In a dried reaction container, mesitylcopper (3.65 mg, 0.020 mmol), (S)-DTBM-segphos (23.8 mg, 0.020 mmol), triethylamine (1.5 mmol, 41.8 µL), and an imine of a raw material (0.20 mmol, 64.2 mg) were added, and the obtained mixture was cooled to −40° C. A 1.2 M solution of borate enolate in THF (1.0 mL, 1.2 mmol) was added thereto, and while stirring the obtained mixture at −40° C., a 0.2 M solution of 4-methoxyphenol (0.20 mmol, 24.8 mg) in THF was slowly added dropwise over 12 hours. The obtained mixture was stirred at −40° C. for another 12 hours to obtain a δ-amino-β-hydroxyaldehyde.

The δ-amino-β-hydroxyaldehyde was derived to an aminodiol, and a yield and diastereoselectivity were determined. To the reaction mixture, lithium borohydride (2 M THF solution, 2.0 mL) was added, and the temperature was gradually raised to 0 degrees. To the reaction mixture, a 1 M aqueous solution of hydrochloric acid (2.0 mL) was added, and extraction was carried out with ethyl acetate. The solvent was then distilled off in vacuo, and an aminodiol was obtained with a yield of 75% and a diastereoselectivity of >20:1 (the ratio of main diastereomer:all the other diastereomers) by silica gel column chromatography (hexane: ethyl acetate=3:2 to 2:3). Selectivity was measured by HPLC (Daicel IA column, 254 nm, 1.0 mL/min, hexane: ethanol=20:1), and the enantioselectivity was 99% ee, and the retention time was 16.8 (major) and 23.5 (minor).

Examples 17 to 18

Synthesis of δAmino-β-Hydroxyaldehydes

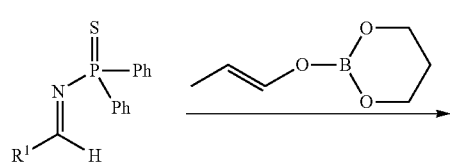

-continued

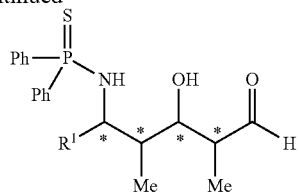

The same operation as in Example 16 was carried out. The results are shown in Table 3.

TABLE 3

| Example | $R^1$ | Yield (%) | Diastereoselectivity (the ratio of main diastereomer:all the other diastereomers) | Enantioselectivity (ee %) |
|---|---|---|---|---|
| 17 | Phenyl | 43 | >20:1 | 99.3 |
| 18 | 4-Bromophenyl | 55 | >20:1 | 99.0 |

INDUSTRIAL APPLICABILITY

The compounds produced in the method of the present invention are useful, for example, as intermediates of medicine, agricultural chemicals, perfume and the like, and the method of the present invention provides an industrially useful production method.

The invention claimed is:

1. A method for producing a compound represented by the following general formula (3):

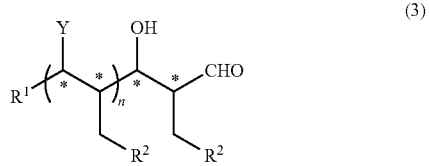

(3)

(wherein, $R^1$ represents an optionally substituted hydrocarbon group, or an optionally substituted heterocyclic group. $R^2$ represents a hydrogen atom or a $C_{1-6}$ alkyl group. Y represents a hydroxy group or NHX (X represents an optionally substituted thiophosphinoyl group). n represents 0 or 1.
* represents an asymmetric carbon atom.),
characterized in that a borate enol ester represented by the following general formula (2):

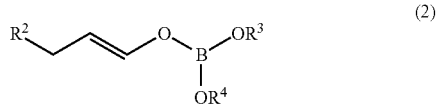

(2)

(wherein, $R^2$ represents a hydrogen atom or a $C_{1-6}$ alkyl group. $R^3$ and $R^4$ each represents a $C_{1-4}$ alkyl group, or $R^3$ and $R^4$ optionally together form a methylene chain which is optionally substituted with alkyl group(s).) is reacted with a compound represented by the following general formula (1):

$R^1CH = Z$ (1)

(wherein, $R^1$ represents an optionally substituted hydrocarbon group or an optionally substituted heterocyclic group. Z represents an oxygen atom or NX (X represents an optionally substituted thiophosphinoyl group.)) in the presence of a copper compound and an optically active bidentate phosphine compound.

2. The method according to claim 1 which further comprises a step of reacting a reaction product produced by the method of claim 1 with a borate enol ester represented by the general formula (2).

3. The method according to claim 1, wherein the borate enol ester of the general formula (2) is obtained by the isomerization reaction of the following scheme using an iridium catalyst:

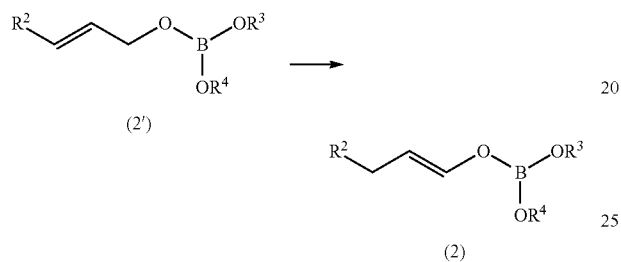

(wherein, in the scheme, $R^2$ represents a hydrogen atom or a $C_{1-6}$ alkyl group. $R^3$ and $R^4$ each represents a $C_{1-4}$ alkyl group, or $R^3$ and $R^4$ optionally together form a methylene chain which is optionally substituted with alkyl group(s)).

4. The method according to claim 1, wherein the optically active bidentate phosphine compound is a phosphine compound represented by the following general formula (4):

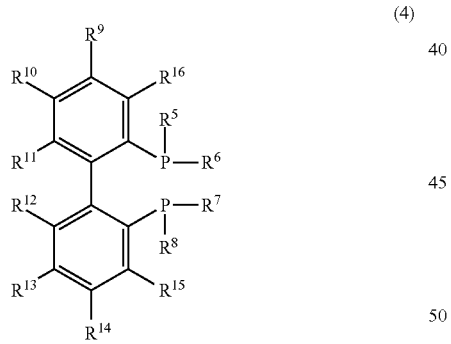

(wherein, in the formula (4), $R^5$, $R^6$, $R^7$ and $R^8$ each independently represent a phenyl group, a cyclopentyl group or a cyclohexyl group which is optionally substituted with substituent(s) selected from the group consisting of an alkyl group, an alkoxy group and a halogen atom. $R^9$, $R^{10}$, $R^{11}$, $R^{12}$, $R^{13}$, $R^{14}$, $R^{15}$ and $R^{16}$ may be the same or different from one another, and each represents a hydrogen atom, an optionally substituted alkyl group, an alkoxy group, an acyloxy group, a halogen atom, a haloalkyl group or a dialkylamino group, or $R^{10}$ and $R^{11}$, and $R^{12}$ and $R^{13}$ optionally together form an optionally substituted methylene chain or an optionally substituted alkylenedioxy group, with the proviso that $R^{11}$ and $R^{12}$ are not a hydrogen atom).

5. The method according to claim 2, wherein the borate enol ester of the general formula (2) is obtained by the isomerization reaction of the following scheme using an iridium catalyst:

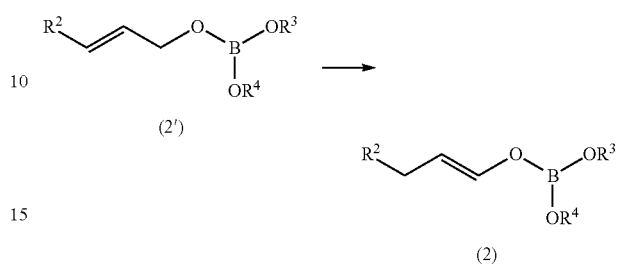

(wherein, in the scheme, $R^2$ represents a hydrogen atom or a $C_{1-6}$ alkyl group. $R^3$ and $R^4$ each represents a $C_{1-4}$ alkyl group, or $R^3$ and $R^4$ optionally together form a methylene chain which is optionally substituted with alkyl group(s)).

6. The method according to claim 2, wherein the optically active bidentate phosphine compound is a phosphine compound represented by the following general formula (4):

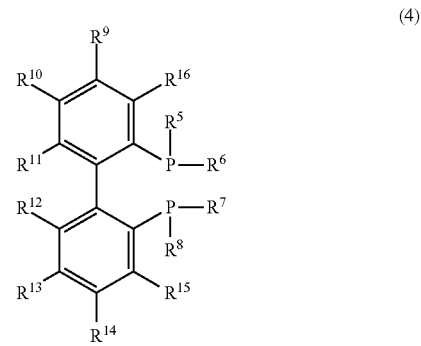

wherein, in the formula (4), $R^5$, $R^6$, $R^7$ and $R^8$ each independently represent a phenyl group, a cyclopentyl group or a cyclohexyl group which is optionally substituted with substituent(s) selected from the group consisting of an alkyl group, an alkoxy group and a halogen atom. $R^9$, $R^{10}$, $R^{11}$, $R^{12}$, $R^{13}$, $R^{14}$, $R^{15}$ and $R^{16}$ may be the same or different from one another, and each represents a hydrogen atom, an optionally substituted alkyl group, an alkoxy group, an acyloxy group, a halogen atom, a haloalkyl group or a dialkylamino group, or $R^{10}$ and $R^{11}$, and $R^{12}$ and $R^{13}$ optionally together form an optionally substituted methylene chain or an optionally substituted alkylenedioxy group, with the proviso that $R^{11}$ and $R^{12}$ are not a hydrogen atom.

7. The method according to claim 3, wherein the optically active bidentate phosphine compound is a phosphine compound represented by the following general formula (4):

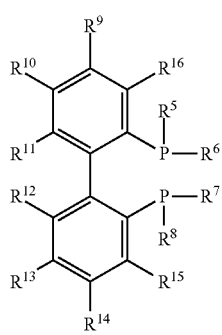
(4)

wherein, in the formula (4), $R^5$, $R^6$, $R^7$ and $R^8$ each independently represent a phenyl group, a cyclopentyl group or a cyclohexyl group which is optionally substituted with substituent(s) selected from the group consisting of an alkyl group, an alkoxy group and a halogen atom. $R^9$, $R^{10}$, $R^{11}$, $R^{12}$, $R^{13}$, $R^{14}$, $R^{15}$ and $R^{16}$ may be the same or different from one another, and each represents a hydrogen atom, an optionally substituted alkyl group, an alkoxy group, an acyloxy group, a halogen atom, a haloalkyl group or a dialkylamino group, or $R^{10}$ and $R^{11}$, and $R^{12}$ and $R^{13}$ optionally together form an optionally substituted methylene chain or an optionally substituted alkylenedioxy group, with the proviso that $R^{11}$ and $R^{12}$ are not a hydrogen atom.

8. The method according to claim 5, wherein the optically active bidentate phosphine compound is a phosphine compound represented by the following general formula (4):

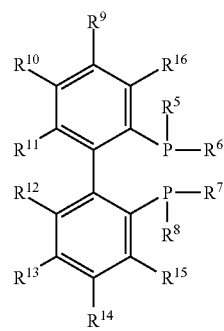
(4)

wherein, in the formula (4), $R^5$, $R^6$, $R^7$ and $R^8$ each independently represent a phenyl group, a cyclopentyl group or a cyclohexyl group which is optionally substituted with substituent(s) selected from the group consisting of an alkyl group, an alkoxy group and a halogen atom. $R^9$, $R^{10}$, $R^{11}$, $R^{12}$, $R^{13}$, $R^{14}$, $R^{15}$ and $R^{16}$ may be the same or different from one another, and each represents a hydrogen atom, an optionally substituted alkyl group, an alkoxy group, an acyloxy group, a halogen atom, a haloalkyl group or a dialkylamino group, or $R^{10}$ and $R^{11}$, and $R^{12}$ and $R^{13}$ optionally together form an optionally substituted methylene chain or an optionally substituted alkylenedioxy group, with the proviso that $R^{11}$ and $R^{12}$ are not a hydrogen atom.

* * * * *